United States Patent [19]

Brenman et al.

[11] Patent Number: 4,542,753

[45] Date of Patent: Sep. 24, 1985

[54] APPARATUS AND METHOD FOR STIMULATING PENILE ERECTILE TISSUE

[75] Inventors: Henry S. Brenman, Cinnaminson; Philip Katz, Princeton Junction, both of N.J.; Harold L. Schwartz, King of Prussia, Pa.

[73] Assignee: Biosonics, Inc., Philadephia, Pa.

[21] Appl. No.: 452,119

[22] Filed: Dec. 22, 1982

[51] Int. Cl.$^4$ .......................... A61N 1/04; A61N 1/36
[52] U.S. Cl. .................................. 128/788; 128/421; 128/741; 29/825
[58] Field of Search ............... 128/788, 421, 741, 639; 264/222, DIG. 30; 29/825, 835, 844

[56] References Cited

U.S. PATENT DOCUMENTS

| | | | |
|---|---|---|---|
| 2,808,834 | 10/1957 | Marden | 128/419 S |
| 2,932,297 | 4/1960 | Provenza | 128/419 S |
| 3,403,684 | 10/1968 | Stiebel et al. | 128/788 |
| 3,874,373 | 4/1975 | Sobel | 128/49 |
| 3,933,147 | 1/1976 | DuVall et al. | 128/788 |
| 3,941,136 | 3/1976 | Bucalo | 128/422 |
| 3,954,102 | 5/1976 | Buuck | 128/79 |
| 4,124,028 | 11/1978 | Gallo | 128/419 R |
| 4,267,838 | 5/1981 | McCall | 128/789 |
| 4,387,719 | 6/1983 | Plevnk et al. | 128/421 |

FOREIGN PATENT DOCUMENTS 0565468 11/1958 Canada ............................... 128/788

OTHER PUBLICATIONS

Dziuk et al., "The Technique of Electroejaculation and its use in Dairy Bulls", Univ. of Minn. Scientific Journal, 1954.

Blackshaw, "A Bipolar Rectal Electrode for the Electrical Production of Ejaculation in Sheep", Australian Veterinary Journal, 8/1954.

Healey et al., "The Construction of Rectal Electrodes for Electroejaculation", Journal Reprod. Fert., 11, 299–301, 1966.

*Primary Examiner*—Lee S. Cohen
*Assistant Examiner*—Steven Falk
*Attorney, Agent, or Firm*—Robert C. Podwil

[57] ABSTRACT

A stimulator for penile erection comprises a body member which may be inserted into the rectum of a user, the body member being so shaped as to closely conform to the topological configuration of the rectum from the anal area to a site adjacent to the prostate gland. Within the body member is electrical circuitry for generating a neurally stimulating electrical signal. Electrodes, placed at particular locations on the surface of the body member, apply the signal to the user. At least one of the electrodes closely contacts the prostate gland when the body member is operatively disposed, at a region or spot on the prostate gland previously determined to be sensitive to electrical stimulation. Also disclosed is a method for making the aforesaid body member by taking an impression of the rectum of the user, and a method for inducing penile erection which includes the steps of locating sensitive regions or spots on the prostate gland, and applying electrical stimulation directly to those spots so as to induce erection.

21 Claims, 11 Drawing Figures

4,542,753

APPARATUS AND METHOD FOR STIMULATING PENILE ERECTILE TISSUE

BACKGROUND OF THE INVENTION

This invention relates to apparatus and a method for applying electrical energy to living tissue, and more particularly, to apparatus and a method for stimulating penile erectile tissue and a method of making such apparatus.

As is well known, the erectile tissue of the penis is composed of hollow sinuses, the walls of which contain involuntary muscle tissue. Blood reaches the sinuses through arterioles and capillaries, and the outlets from the sinuses are also controlled by involuntary muscle. In erection, impulses from the pelvic nerve cause dilation of the arterioles and constriction of the involuntary muscle controlling the outlets from the sinuses. The combined effect of these actions is to dilate the vascular spaces and to create high pressure within them, causing hardening and erection of the organ.

Normal erection is dependent upon a complex interaction of psychological, neurological and vascular factors. Failure of any of them can result in an inability to sustain erection, a condition commonly referred to as male impotence.

It has been suggested that, in the case of individuals whose impotence is a result of certain neurological deficits, the application of external electrical stimulus may ameliorate the impotence. Thus, for example, in U.S. Pat. No. 3,403,684, issued Oct. 1, 1968, to Stiebel, et al., a device was suggested in which a pair of electrodes were placed in the area of the prostate gland of a user, and it was proposed that an electrical signal be applied to the electrodes to cause electrical stimulation of the surrounding tissues.

It has now been demonstated in laboratory animals that stimulation can best be accomplished by applying an electrical stimulus as directly as possible to certain highly sensitive and identifiable areas of the prostate gland. It is believed that if the signal is applied to these areas, the precise locations of which will vary from individual to individual, the nature of the signal is less critical than was formerly thought, and the desired results can be consistently and reliably obtained.

It is, therefore, a general object of this invention to provide apparatus and a method for stimulating erectile tissue, and more particularly apparatus and a method which are useful to promote penile erection by electrical stimulation.

Another object of this invention is to provide a method of making apparatus for stimulating penile erection, and it is still another object of the invention to provide a genital stimulator which is compact, self-contained, and capable of being accurately placed and positioned for use.

Another object of this invention is to provide a genital stimulator which is maintained in position for use by the anatomical structures, particularly the musculature, which surround it when it is positioned for use.

Other objects will appear hereinafter.

The foregoing and other objects are realized, in a presently preferred form of the apparatus, by a stimulator which comprises a body member, the shape of which is determined by an impression molded in situ, and which is adapted for insertion into the rectum of a user. Molding in the above manner ensures that the body member is so configured as to closely conform to the unique configuration of the rectum of each user. Within the body member there is placed a highly miniaturized electrical signal generator, and electrodes are disposed at carefully selected localities on the outer surface of the body member. In accordance with the present invention, at least one electrode is juxtaposed as closely as possible to a selected spot on the prostate of the user which has been determined to be sensitive to electrical stimulation. Close conformity of the body member to the configuration of the rectum of the user, as well as a unique homeostatic effect described below, maintains the electrode in close proximity to the sensitive spot, and assures application of electrical impulses to that spot to stimulate erection. Electrical signals are generated by signal generating circuitry disposed within a cavity in the body member, and the body member, signal generating circuitry and its associated power supply are self-contained. Actuation of the apparatus may be by means of a manually operated or magnetically activated switch associated with the body member, or by remote telemetric means.

In its method aspect, the present invention involves palpation of the prostate gland of a potential user and application to the prostate, at selected spots, of an electrical impulse. The result of the application of the impulse at the selected spot can be sensed or observed, and determines for the clinician the efficacy of application of electrical stimulus to that spot. When the sensitive spot or spots of the prostate have been identified, an impression is taken of the rectum of the user in at least the region extending from the anus to a location proximate to the prostate gland, and from that impression, a body member closely conforming to the shape of the rectum can be made. Electrodes are positioned on the body member at locations corresponding to the previously identified sensitive spot or spots, and at other locations which provide suitable electrical contact with the tissues of the user.

The method of making the apparatus involves the taking of an impression of the rectum of the potential user by inserting into the rectum a sheath; injecting a molding composition into the sheath; permitting the molding composition to become somewhat hard; withdrawing the sheath slightly and permitting the composition to further harden; and then removing the sheath and the impression when the composition has fully hardened. The hardened composition thus forms an impression closely conforming to the configuration of the rectum, from which the body member of the apparatus may be molded. Electrodes can then be applied to the body member in positions corresponding to the sensitive spots on the prostate as earlier determined by palpation and stimulation, and electrical circuitry may be placed within the body member to produce the above-described apparatus.

There are seen in the drawings forms of the invention which are presently preferred (and which represent the best mode contemplated for carrying the invention into effect), but it should be understood that the invention is not limited to the precise arrangements and instrumentalities shown.

DETAILED DESCRIPTION

Figure 1:
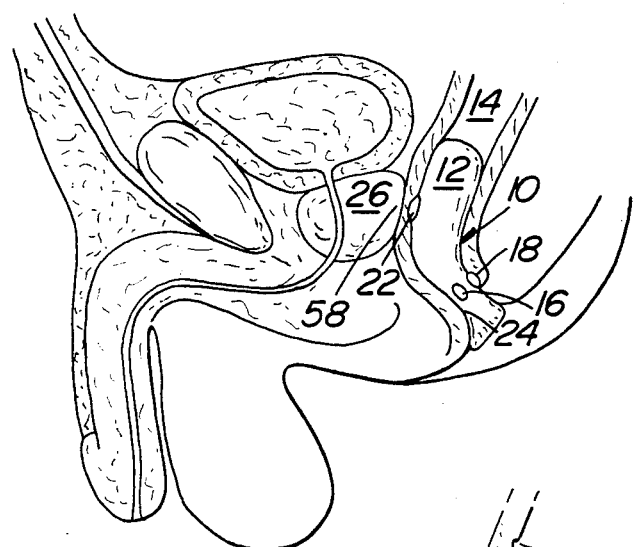
FIG. 1 is a cross-sectional view, showing apparatus in accordance with the invention operatively disposed in the rectum of a user.
Figure 3:
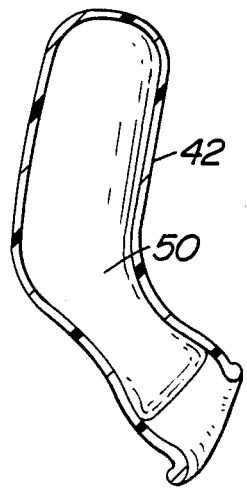
FIG. 3 is another view depicting aspects of a method of making apparatus in accordance with the invention.
Figure 6:
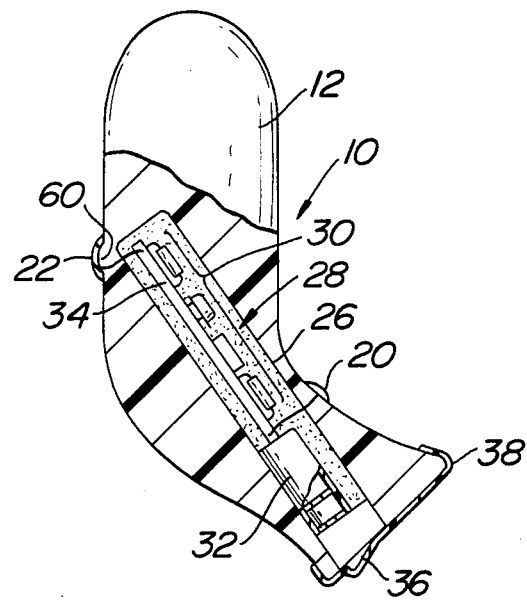
FIG. 6 is a view, partly broken away, showing certain structural details of apparatus in accordance with the invention.
Figure 7:
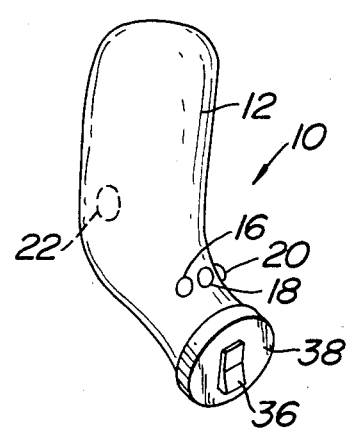
FIG. 7 is a pictorial view of one form of apparatus in accordance with the invention.

Referring now to the drawings in detail, wherein like reference numerals indicate like elements, there is seen in FIGS. 1, 6 and 7, stimulator apparatus designated generally by the reference numeral 10.

The apparatus 10 comprises a body member 12, adapted, as is best seen in FIG. 1, for insertion into the rectum 14 of a user. The shape of the body member 12 is unique to each user, and is arrived at by molding in situ, in a manner described in detail below.

Disposed on the outer surface of the body member 12 are electrodes which are so positioned that when the body member 12 is properly disposed within the rectum 14 they intimately contact the mucosa of the rectum and adjacent structures. The electrodes comprise, in the illustrated embodiment, three ground electrodes, 16, 18 and 20, and what may be referred to conveniently as an active electrode 22. As is best seen in FIG. 1, the electrodes 16, 18 and 20 confront the anal sphincter 24 of the user. The active electrode 22 intimately contacts the rectal wall, in juxtaposition to and in close contact with a critical region of the prostate gland 26.

Referring to FIG. 6, it will be seen that the body member 12 has an internal cavity 28, in which there is housed electrical and electronic components and circuitry designated generally by the reference numeral 30. In general, the electrical and electronic components include a highly miniaturized and self-contained signal generator with associated control circuitry, and a power supply 32, all associated with a compact printed circuit board 34.

Figure 8:
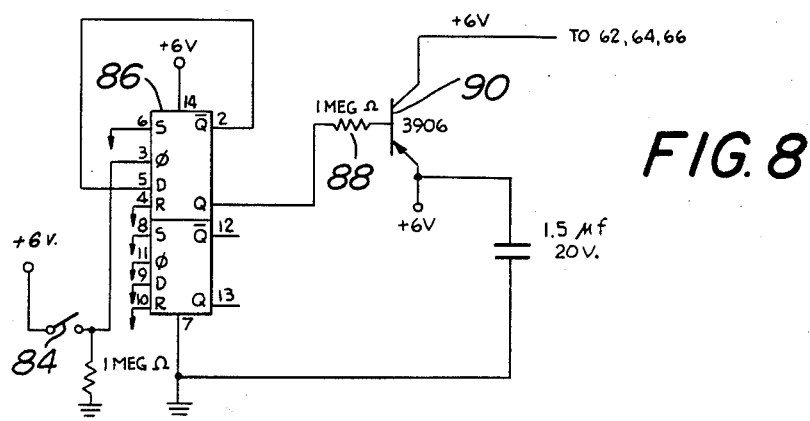
FIGS. 8, 9 and 10 are schematic diagrams illustrating exemplary electronic circuit means for use in the present invention.

Referring now to FIGS. 6 and 7, the electrical and electronic components 28 may include an off-on switch 36, to activate the apparatus 10. In one form of the apparatus 10, in which the switch 36 is manually operable, the switch 36 is disposed in an end wall 38 of the body member 12, and is accessible for manipulation when the apparatus 10 is operatively disposed. As an alternative, the apparatus 10 may be activated by means of a radio frequency or other remote signal. FIG. 8 illustrates an alternative switching and latching circuit, which serves (as does the manual switch 36) to activate the apparatus 10, placing the circuitry in an "on" condition and "latching" the circuitry 30 in that condition as long as desired. Referring again to FIGS. 6 and 7, the switch 36 may be encased within a flexible, liquid impervious end seal 38, sufficiently thin to permit ready manipulation of the switch 36 by applying external pressure to the end seal 38.

Figure 2:
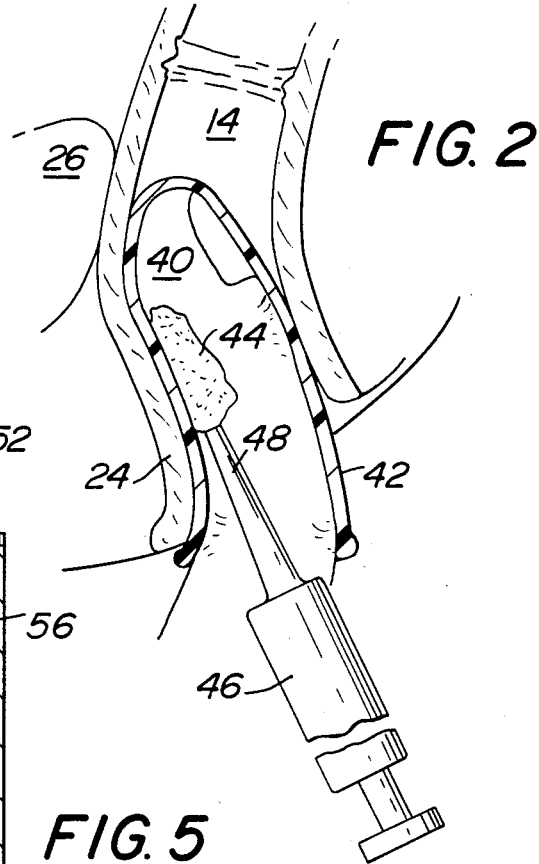
FIG. 2 is a partial cross-sectional view, depicting aspects of the method by which apparatus in accordance with the present invention may be fitted to a user.

Referring now to FIGS. 2 through 5, a presently preferred technique or method by which the body member 12 may be molded is illustrated. Referring first to FIG. 2, a finger 40 of a clinician or technician is placed in a flexible chemically inert sheath 42. The sheath 42 for this purpose may be an ordinary condom. The finger 40, encased in the sheath 42 is inserted intra-anally to a depth of perhaps 10 cm., to a point at which the prostate 26 may be palpated. Molding composition 44, contained in a syringe 46 whose tip 48 projects into the sheath 42, may now be injected into the sheath 42, thus filling the sheath and causing the sheath 42 to expand within the rectum 14. The molding composition 44 injected into the sheath 42, it has been found, can be of the kind known as Alginate or its equivalent, commonly used to make dental impressions. Such a material is prepared from a powder and water mixture, and, depending upon temperature, becomes firm but not rigid in about three to five minutes. The molding composition 44, once inserted into the sheath 42 is allowed to become semi-rigid, and the sheath 42 is drawn rearwardly through the anus to a small extent so tha anal sphincter 24 tends to compress the rigidifying mass. has been found that, at this stage of the procedure, application of topical electrical stimulation to the area (on the order of about 3 v.) causes contraction the musculature of the anal area so as to create an accurate and detailed outline of the configuration of the rectum 14. The sheath 42 is next left in position and the molding composition 44 is permitted to harden to form a plug-like mass 50 which cioseiy conforms to the configuration of the subject's rectum and anus.

Figure 4:
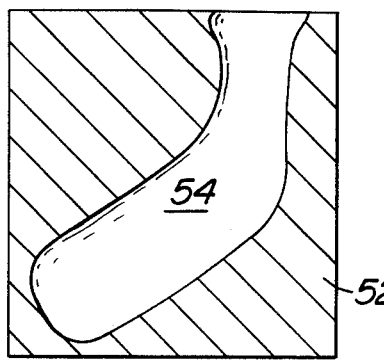
FIG. 4 is a cross-sectional view of a female mold used in a method of making apparatus in accordance with the invention.

Referring now to FIG. 4, the mass 50 may be used, in a conventional manner, to make a female mold 52, and from the female mold 52 may be made any number of duplicates of the mass 50. The duplicates may be made from plaster, dental stone, epoxy or vinyl molding compounds of numerous kinds as well as methyl methacrylate (acrylic). The mass 50 may be inserted into the rectum 14 and used to determine the position of the electrodes in a manner to be described below.

Figure 5:
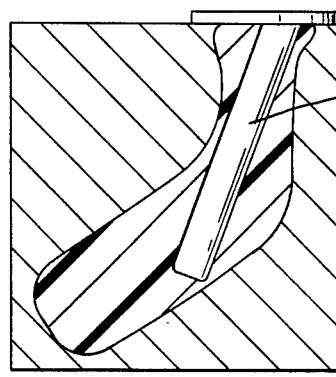
FIG. 5 is a cross-sectional view, depicting another step in the method of making apparatus in accordance with the invention.

Referring to FIG. 5, the female mold 52 may be used to mold the final form of the body member 12. In the molding of the body member 12, the cavity 54 of the female mold 52 is partly filled by a core 56 suspended within the cavity 54. Material suitable for the body member 12 includes castable plastic polymeric materials, such as methylmethacrylate. This material, like other suitable materials, is chemically inert and usable in the body.

The material of the female mold 52, it should be understood, is of rubber-like composition, which can be deformed to permit removal of the molded article from the cavity 54. As an alternative, the female mold 52 may be a split mold, halves of which can be separated to free a sharply undercut molded article. Removal of the core 56 from the molded article yields a body of the kind shown in FIG. 6, which includes a cavity 26 whose shape conforms to the core 56.

The electrodes 16, 18, 20 and 22 may now be applied to the body member 12. The electrode 22 is so positioned on the body member 12 that when the body member 12 is properly placed within the rectum, the electrode 22 is juxtaposed to a previously-determined sensitive spot 58 of the prostate 26, seen in FIG. 1. The electrodes 16, 18 and 20 are so positioned as to be juxtaposed to the ring defined by the anal sphincter 24, and are grasped by the anus. The body member 12 may be provided, when molded, with projections 60 (one of which is seen in FIG. 6) at locations corresponding to the locations of the electrodes 16, 18, 20 and 22. This may be accomplished by appropriately adding material to the mass 50 or removing it from the female mold 52. The electrodes themselves may advantageously be "dished" to conform to the projections 60, and to present a convex outer surface which enhances electrical contact with surrounding tissues. The electrodes 16, 18, 20 and 22 may be of platinum or other suitable conductive, inert, non-polarizing material affixed to the body member 12 by suitable adhesives.

An important aspect of the invention is the manner in which the body member 12 with its associated electrodes is held in position by the configuration of the rectum. The above-described molding technique, which yields a body member 12 closely conforming to the shape of the rectum, causes the body member 12, when positioned within the rectum, to be constrained against either rotation or movement axially with respect to the anal orifice. Thus, the body member 12, and consequently the electrodes 16, 18, 20 and 22 are maintained by the anal cleft and the shape of the rectum 14 in a desired orientation with respect to the prostate gland 26. The above-described steps of allowing the molding composition 44 to become semi-rigid and then drawing the sheath 42 through the anus to a small extent assure that the impression defined by the mass 54 encompasses regions within the rectum 14 and also regions external of the anus. Contact between the body member 12 and the irregularly configured surrounding structures tends to maintain the body member 12 in precisely the desired position. The body member 12 may also be made with a roughened surface, to minimize any tendency of the apparatus 10 to shift with respect to the surrounding structures.

Identification of the spot or spots to be stimulated by the apparatus 10 is accomplished by applying to the prostate gland 26 electrical energy which simulates the erection-stimulating signal ultimately to be produced by the apparatus 10. Such applications, when made at sensitive spots, cause palpable or visible physical reactions which are signs of incipient erection. The presently preferred technique for locating sensitive spots is the use of glove-mounted electrodes of the kinds described in co-pending application, Ser. No. 452,319 filed Dec. 22, 1982, for "MEANS FOR APPLYING ELECTRICAL STIMULI TO LIVING TISSUE" (assigned to the assignee of the present application), and illustrated in FIG. 11 herein. It has been found in laboratory animals that the application of electrical stimuli to critical spots of the prostate yields the desired result, while other regions show relative insensitivity to the application of the stimulus. As has been explained, advantages of the present apparatus and method flow from the ability of the apparatus 10 to apply energy directly to only those specific regions which have been ascertained to provide the desired result. When desirable spots have been identified and noted, the desired locations of electrodes such as the electrode 22 on the body member 12 may be ascertained by measurement, so that when the apparatus 10 is positioned for use, the active electrodes are proximal the efficacious spots on the user's prostate gland. As indicated above, the unique shape of the body member 12, cooperating with key anatomical landmarks, serves to maintain the apparatus 10 in precisely the desired orientation with respect to the rectum and prostate gland, so that the electrodes are maintained in close contact with the anatomical structures adjacent to which they are placed. In humans, the anatomical landmarks which maintain the apparatus 10 in position include the anal cleft, the configuration and angular orientation of the anal sphincter, and the position and configuration of the prostate gland itself.

A unique characteristic of the apparatus 10, which has been observed in laboratory animals, is its tendency to induce in the anatomical structures surrounding it forces which tend to restore the apparatus 10 and its associated electrodes to their desired positions. In other words, it has been found that the apparatus 10 creates what may be characterized as a self-restorative or homeostatic force, by electromechanical feedback resulting from displacement of the apparatus 10. This effect, it is theorized, is due to the fact that transient lateral displacement of an electrode such as the electrode 22 results in the application of electrical energy to the tissues contacted by the displaced electrode. This, it has been found, results in contraction of localized myofibers in those specific areas, and such contractions, due to the shape of the body member 12 and the surrounding anatomy tend to urge the apparatus 10 and electrode 22 to their original and desired positions. This homeostatic mechanism aids the above-described interaction between the shape of the body member 12 and surrounding anatomical landmarks to maintain the apparatus 10 and the electrodes in their desired positions.

Figures 9, 11:
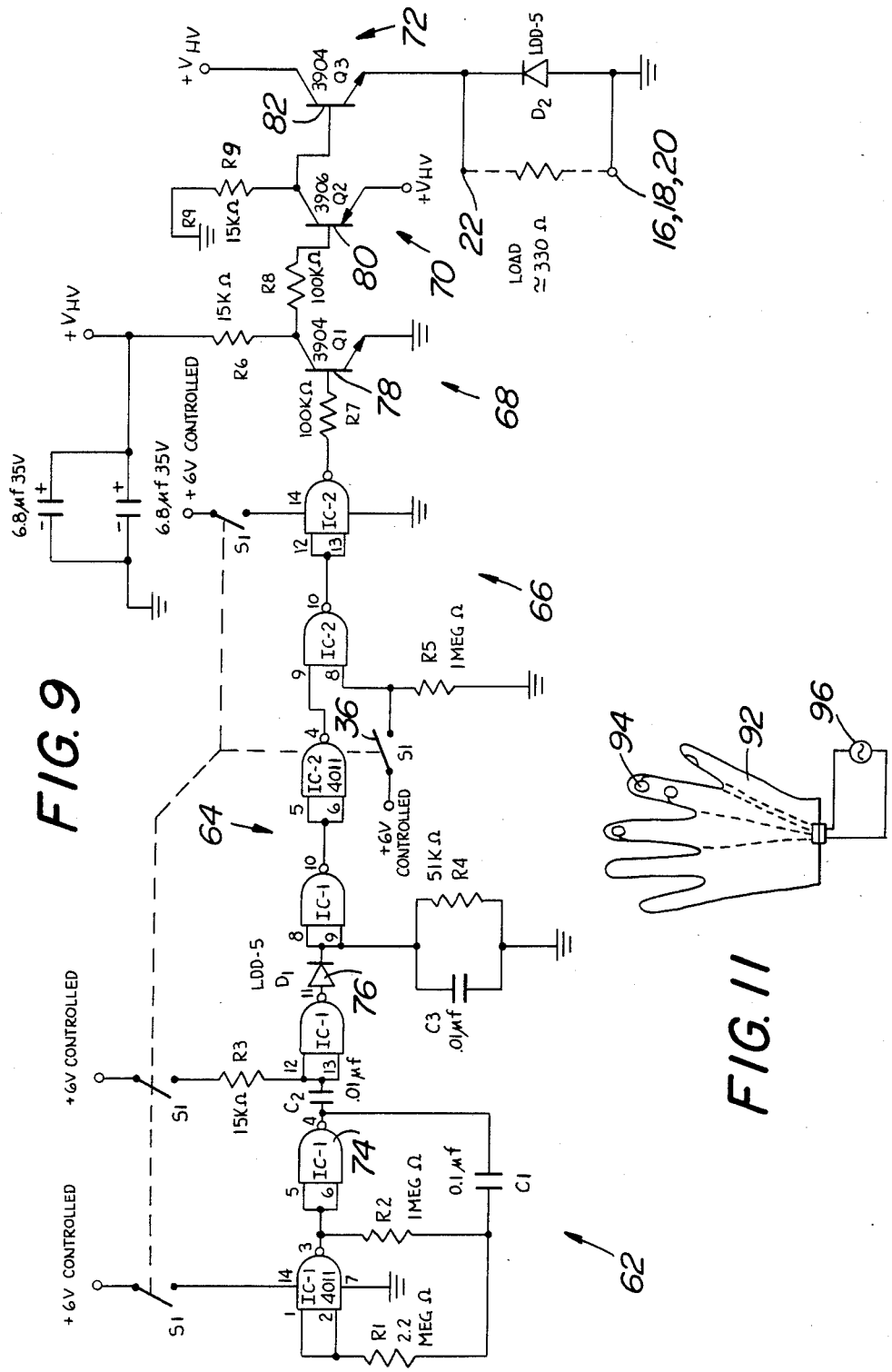
FIG. 11 illustrates apparatus which may conveniently be used for palpation and stimulation in practicing the present invention.

FIG. 9 illustrates a presently preferred electronic circuit by which stimulating signals can be produced, although other specific circuitry may perform the same function. The illustrated circuitry includes an astable multivibrator, designated generally by the reference numeral 62; a monostable multivibrator, designated generally by the reference numeral 64; NAND gating 66, the purpose of which will be described below; two inverters 68 and 70; and an emitter-follower 72 providing a "high" voltage (about 20 volts) output.

The power supply 32 in the presently preferred form of the invention is provided by lithium batteries (seen in FIG. 6), maintained in series relationship by a shrink-fitted sleeve as is known in the art. In one form of the invention, the power supply 32 consists of two 3.0 volt batteries, producing six volts, and eight 3.0 volt batteries, providing 24 volts.

The astable multivibrator 62 and monostable multivibrator 64, which comprise the first and second stages of the circuitry 30, provide pulses of approximately six volts, and of a desired pulse-width and frequency. Thus, in the illustrated circuitry 30, the output of the astable multivibrator 62 is a series of square pulses at an amplitude of six volts and a frequency of about 30 to 33 Hz, and the monostable multivibrator 64 serves to shape the pulses to a presently preferred width of 500 microseconds.

The principal components of the illustrated astable and monostable multivibrators 62, 64 are commercially available highly miniaturized integrated circuits. Thus, with reference to the astable multivibrator 62, each of the integrated circuits (labeled "IC-1") are of a type sold by Amperex Electronics Corporation, a subsidiary of North American Phillips Corp., as so-called "leadless inverted devices" ("LIDS"). They are electronically equivalent, however, to standard sized integrated circuits. The integrated circuit 74, for example, in FIG. 9, and the other integrated circuits labeled "IC-1" are "LIDS" equivalent to CMOS No. 4011 integrated circuits available from numerous manufacturers, including, among others, RCA, Texas Instrument Corp., National Semiconductor, and Solid State Scientific. All of the other components in the preferred form of the circuitry 30 are commercially available items. By way of illustration, the diode 76 in one operative form of the circuitry is an Amperex Electronic Corporation Part No. LDD-5. The NPN transistor 78 used in the inverter circuit 68 is an Amperex LDA-404 ("LIDS" equivalent to 2N 3904). The PNP transistor 80 in the inverter 70 is an Amperex LDA-452, equivalent to a 2N 3906. The NPN transistor 82 is also an Amperex LDA-404.

The circuitry 30 illustrated in FIG. 9, as presently contemplated, may use one of two modes of control. In the first mode, perhaps best seen in FIG. 9, manual operation of the switch $S_1$ (the above-mentioned switch 36, seen in FIGS. 6 and 7), applies to the astable multivibrator 62, monostable multivibrator 64, and other aspects of the circuitry 30, the 6 volt supply. An output pulse will be repetitively supplied during the time in which the circuitry 30 is so powered. In other words, stimulation is enabled upon closing of the switch 36 to power the circuit, and stimulation is inhibited when the switch 36 is open.

Referring now to FIG. 8, there is seen an alternative arrangement for enabling stimulation, using an external reed switch 84 to control pulse output, and hence stimulation. The reed switch 84 may advantageously be operated by an external magnet or other remotely operable means, under the control of the user.

The reed switch 84 controls a flip-flop, designated generally by the reference numeral 86, which performs a latching function with respect to the power supply of the circuitry 30. The flip-flop 86 in its presently preferred form, is based upon a LIDS equivalent 4013 integrated circuit (LFF 4013), supplying, through the output resistor 88 a PNP transistor 90 (LDA 452, LIDS equivalent to 2N3906). Because it is of the PNP type, the transistor 90 is "off" when it sees high Q, and when the transistor 90 is off no voltage will be seen at the six volt input of the circuitry 30. It will be appreciated, however, that changing the state of the flip-flop 86 will turn on the six volt supply to the circuitry 30, thus enabling stimulation.

The apparatus illustrated in FIG. 8 thus provides both a latching function (enabling continuous stimulation) and a controlled six volt power supply for the circuitry 30. The circuitry illustrated in FIG. 8 enables the stimulator apparatus 10 to be inserted into or removed from the rectum 14 with assurance that the apparatus 10 is inhibited, thus eliminating undesirable effects such as untimely or unwanted neural stimulation affecting muscle groups other than those involved in penile erection.

Figure 10:
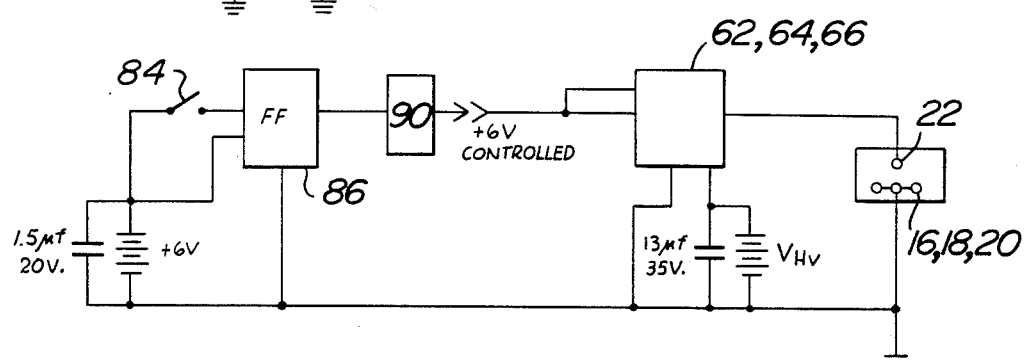

FIG. 10 illustrates diagrammatically the functional interrelationship between the reed switch 84, the flip-flop 86, the signal generating and control circuitry 62, 66, 68 and 72, and the power supply (represented in FIG. 10 by six volt and high voltage sources corresponding to the power supply 32). As can be seen in FIG. 10, closing of the reed switch 84 (by magnetic or remote means) configures the flip-flop 86 to provide to the other circuitry a controlled six volt supply. The other circuitry, in turn provides the stimulating signal and delivers it to the active electrode 22.

The above-described circuitry 30 is designed to drive an output load of approximately 330 ohms (the assumed load resistance based on observations in laboratory animals). When the output pulse is inhibited, the output is zero volts. When the output is enabled, the actual output level is a function of the voltage of the high voltage supply ($V_{hv}$) In one operative embodiment, the high voltage supply provides twenty-four volts, and the output is within 0.5 volts of this voltage and substantially constant for 500 microseconds when driving a 330 ohm load.

Those skilled in the art will appreciate that the high and low voltages, as well as the parameters (pulse width, frequency and wave form) of the output pulse may be varied by conventional circuit elements, perhaps controlled by telemetry. Utilizing appropriate feedback mechanisms, the circuit may be made self-regulating and self-optimizing.

FIG. 11 illustrates, somewhat schematically, a surgical glove 92, to which there are affixed electrodes 94. The electrodes 94 may be electrically connected to a source 96 of electrical energy, such as a signal generating circuit analogous to the above-described circuitry 30. Palpation may thus be done using the glove 92, and stimulation may be accomplished by application of electrical energy through the electrodes 94.

The present invention may be embodied in other specific forms without departing from its spirit and essential attributes and, accordingly, reference should be made to the appended claims rather than the foregoing specification as indicating the scope of the invention.

What we claim is:

1. A stimulator fur use in promoting penile erection by neural stimulation, comprising a body member adapted for insertion into the rectum of a user, said body member being so shaped as to closely conform to the topological configuration of the rectum of a specific user from the anal area to a site adjacent to the prostate gland, said body member having a cavity therein, electrical signal generating means disposed in said cavity, and a plurality of electrodes disposed on the outer surface of said body member and operatively coupled to said signal generating means, at least one of said electrodes being juxtaposed to a selected neurally sensitive spot on the prostate gland of the user when said body member is operatively disposed so as to apply electrical stimulation to the sensitive spot.

2. Apparatus in accordance with claim 1, wherein said signal generating means includes a power supply disposed within said cavity.

3. Apparatus in accordance with claim 2, and switch means associated with said body member for activating said electrical signal generating means.

4. Apparatus in accordance with claim 3, wherein said electrical signal generating means produces a series of pulses having an amplitude of about 20 volts, a duration of about 500 microseconds and a frequency of about 33 Hz.

5. Apparatus in accordance with claim 4, wherein said electrical signal generating means comprises a multivibrator and a power amplifier.

6. Apparatus in accordance with claim 1, wherein said electrodes project outwardly from the surface of said body member so as to ensure intimate contact with the surrounding body tissues of the user.

7. Apparatus in accordance with claim 6, wherein said electrodes are of platinum or other inert, non-polarizing, conducting materials.

8. Apparatus in accordance with claim 1, wherein the shape of said body member conforms to an impression molded in situ so as to assume a shape in close conformity with the topological configuration of the anatomy of the user.

9. Apparatus in accordance with claim 1, wherein said one electrode is an active electrode, and said electrodes comprise at least one other electrode which is so positioned on said body member as to be, when said body member is operatively disposed, in juxtaposition to the anal sphincter of the user.

10. Apparatus in accordance with claim 9, wherein said signal generating means includes a power supply disposed within said cavity, and switch means for enabling said electrical signal generating means.

11. Apparatus in accordance with claim 10, wherein said electrical signal generating means comprises a multivibrator.

12. Apparatus in accordance with claim 11, wherein said electrodes project outwardly from the surface of said body member so as to ensure intimate contact with the surrounding body tissues of the user.

13. Apparatus in accordance with claim 9, wherein said electrodes are of platinum or other inert, non-polarizing, conducting materials.

14. Apparatus in accordance with claim 13, wherein said body member conforms to an impression molded in situ so as to assume a shape in close conformity with the topological configuration of the anatomy of the user.

15. A method for making apparatus for producing penile erection, comprising the steps of palpating and stimulating, the prostate gland of the subject to locate therein neurally sensitive spots susceptible to electrical stimulation, taking an impression of the rectum of a user in at least the region extending from the anus to a location proximate to the prostate gland, forming a body member to closely conform in shape to the topological configuration of the rectum of the subject, and affixing to said body member a plurality of electrodes, at least one of said electrodes being positioned at a location on said body member closely adjacent to a sensitive spot, whereby the application of an electrical signal to said electrodes facilitates application of said signal directly to said sensitive spot.

16. A method in accordance with claim 15, wherein said steps of taking an impression and of forming a body member comprise the further steps of inserting into the rectum of a subject a flexible, chemically inert sheath, injecting into said sheath an amorphous mass of hardenable molding material, permitting said material to become semi-rigid, partly withdrawing said sheath so as to partly distend the anal area and to form an impression thereof in said molding material, allowing said molding material to fully harden, withdrawing said sheath and the material contained therein, stripping said sheath from said hardened material, and molding the body member from the impression provided from said hardened material.

17. A method in accordance with claim 16, wherein said molding material consists essentially of material of the kind commonly used to make dental impressions.

18. A method in accordance with claim 16, wherein said step of molding the body member is so performed as to create a cavity within said body member.

19. A method in accordance with claim 18, wherein said last mentioned step consists of molding said body member using a core, the core forming said cavity.

20. A method of stimulating penile erectile tissue, comprising the steps of palpating and stimulating the prostate gland of a specific subject to identify thereon regions which are sensitive to neural stimulation by electrical means, locating said regions, placing in the rectum of the subject means for applying a stimulating signal directly to said regions, and applying said signal directly to at least one of said regions.

21. A method in accordance with claim 20, wherein said steps of palpating and stimulating are performed by applying to said regions an electrical signal.

* * * * *